(12) United States Patent
Wright

(10) Patent No.: US 6,486,220 B1
(45) Date of Patent: Nov. 26, 2002

(54) REGENERATION PROCEDURE FOR FISCHER-TROPSCH CATALYST

(75) Inventor: Harold A. Wright, Ponca City, OK (US)

(73) Assignee: Conoco Inc., Houston, TX (US)

( * ) Notice: Subject to any disclaimer, the term of this patent is extended or adjusted under 35 U.S.C. 154(b) by 0 days.

(21) Appl. No.: 09/713,051

(22) Filed: Nov. 15, 2000

Related U.S. Application Data

(60) Provisional application No. 60/166,020, filed on Nov. 17, 1999.

(51) Int. Cl.$^7$ .......................... C07C 27/00; B01J 20/34
(52) U.S. Cl. ................... 518/709; 518/700; 518/715; 518/721; 502/20
(58) Field of Search ................ 518/700, 709, 518/715, 721; 502/20

(56) References Cited

U.S. PATENT DOCUMENTS

| | | | |
|---|---|---|---|
| 2,415,861 A | 8/1947 | Brown et al. ............... 260/666 |
| 2,453,035 A | 12/1948 | Wobker ....................... 196/52 |
| 2,500,519 A | 3/1950 | Clark ........................ 260/449.6 |
| 2,518,775 A | 8/1950 | Guyer ........................ 260/449.6 |
| 2,564,985 A | 8/1951 | Mayland ................... 260/449.6 |
| 2,719,130 A | 9/1955 | Stewart ...................... 252/373 |
| 2,735,802 A | 2/1956 | Jahnig ........................ 196/52 |
| 3,958,957 A | 5/1976 | Koh et al. ................... 48/197 |
| 4,151,190 A | 4/1979 | Murchison et al. ......... 260/449 |
| 4,197,418 A | 4/1980 | Lee et al. ................... 585/469 |
| 4,585,798 A | 4/1986 | Beuther et al. ............. 518/715 |
| 4,595,703 A | 6/1986 | Payne et al. ................ 518/715 |
| 4,600,499 A | 7/1986 | Hettinger, Jr. ............. 208/113 |
| 4,606,811 A | 8/1986 | Hettinger .................... 208/108 |
| 4,738,948 A | 4/1988 | Iglesia et al. ............... 502/326 |
| 4,744,883 A | 5/1988 | Hettinge, Jr. .............. 208/108 |
| 4,822,824 A | 4/1989 | Iglesia et al. ............... 518/709 |
| 4,978,689 A | * 12/1990 | Bell et al. ................... 518/709 |
| 5,260,239 A | 11/1993 | Hsia ............................ 502/30 |
| 5,268,344 A | 12/1993 | Pedrick et al. .............. 502/30 |
| 5,283,216 A | 2/1994 | Mitchell ...................... 502/30 |
| 5,356,845 A | 10/1994 | Clavenna et al. ........... 502/21 |
| 5,397,806 A | 3/1995 | Soled et al. ................ 518/715 |
| 5,545,674 A | 8/1996 | Behrmann et al. .......... 518/715 |
| 5,728,918 A | 3/1998 | Nay et al. ................... 585/733 |
| 5,811,468 A | 9/1998 | Chang et al. ............... 518/700 |
| 5,817,701 A | 10/1998 | Leviness et al. ............ 518/700 |
| 5,817,702 A | 10/1998 | Behrmann et al. .......... 518/700 |
| 5,821,270 A | 10/1998 | Chang et al. ............... 518/700 |
| 5,844,005 A | 12/1998 | Bauman et al. ............. 518/700 |
| 5,929,126 A | 7/1999 | Koveal et al. .............. 518/709 |
| 5,958,986 A | 9/1999 | Mart et al. .................. 518/709 |
| 5,973,012 A | 10/1999 | Behrmann et al. .......... 518/700 |
| 6,022,755 A | 2/2000 | Kinnari et al. .............. 438/53 |
| 6,066,679 A | 5/2000 | Leviness et al. ............ 518/709 |
| 6,068,760 A | 5/2000 | Benham et al. ............. 208/950 |
| 6,107,353 A | 8/2000 | Koveal et al. .............. 518/705 |

FOREIGN PATENT DOCUMENTS

| | | | |
|---|---|---|---|
| CA | 94203562.7 | 12/1997 | |
| EP | 0 220 343 A | 5/1987 | ............ B01J/23/84 |
| EP | 0 363 537 A | 4/1990 | ............ B01J/23/74 |
| GB | 2 222 531 | 3/1990 | ............ B01J/23/90 |
| GB | 2 258 826 | 2/1993 | ............ B10J/23/94 |
| WO | WO 97/17137 | 5/1997 | ............ B10J/37/18 |

OTHER PUBLICATIONS

PCT International Search Report for Application No. PCT/US00/31559, Dated Mar. 29, 2001; (5 p.).

* cited by examiner

*Primary Examiner*—Jafar Parsa
(74) *Attorney, Agent, or Firm*—Conley, Rose & Tayon

(57) ABSTRACT

A process is disclosed for regenerating catalyst used in a process for synthesizing hydrocarbons. The synthesis process involves contacting a feed stream comprising hydrogen and carbon monoxide with a catalyst in a reaction zone maintained at conversion-promoting conditions effective to produce an effluent stream comprising hydrocarbons. The regeneration. process comprises contacting a deactivated Fischer-Tropsch catalyst with a steam under regeneration-promoting conditions, for a period of time sufficient to reactivate the Fischer-Tropsch catalyst.

25 Claims, 1 Drawing Sheet

US 6,486,220 B1

REGENERATION PROCEDURE FOR FISCHER-TROPSCH CATALYST

CROSS-REFERENCE TO RELATED APPLICATIONS

The present application claims the benefit of 35 U.S.C. 111(b) provisional application Ser. No. 60/166,020, filed Nov. 17, 1999, and entitled Regeneration Procedure for Fischer-Tropsch Catalyst.

STATEMENT REGARDING FEDERALLY SPONSORED RESEARCH OR DEVELOPMENT

Not applicable.

FIELD OF THE INVENTION

The present invention relates to a process for the preparation of hydrocarbons from synthesis gas, (i.e., a mixture of carbon monoxide and hydrogen), typically labeled the Fischer-Tropsch process. More particularly, the present invention relates to a regeneration method for a Fischer-Tropsch catalyst. Still more particularly, the present invention relates to the use of steam to decoke and regenerate deactivated Fischer-Tropsch catalyst.

BACKGROUND OF THE INVENTION

Large quantities of methane, the main component of natural gas, are available in many areas of the world. However, most natural gas is situated in areas that are geographically remote from population and industrial centers. The costs of compression, transportation, and storage make the use of this remote gas economically unattractive. To improve the economics of natural gas use, much research has focused on the use of methane as a starting material for the production of higher hydrocarbons and hydrocarbon liquids.

As a result, various technologies for the conversion of methane to hydrocarbons have evolved. The conversion is typically carried out in two steps. In the first step methane is reformed with water or partially oxidized with oxygen to produce carbon monoxide and hydrogen (i.e., synthesis gas or syngas). In a second step, the syngas is converted to hydrocarbons.

This second step, the preparation of hydrocarbons from synthesis gas is well known in the art and is usually referred to as Fischer-Tropsch synthesis, the Fischer-Tropsch process, or Fischer-Tropsch reaction(s). The Fischer-Tropsch reaction involves the catalytic hydrogenation of carbon monoxide to produce a variety of products ranging from methane to higher aliphatic alcohols. The methanation reaction was first described in the early 1900's, and the later work by Fischer and Tropsch dealing with higher hydrocarbon synthesis was described in the 1920's.

Catalysts for use in such synthesis usually contain a catalytically active metal of Groups 8, 9, 10 (in the New notation of the periodic table of the elements, which is followed throughout). In particular, iron, cobalt, nickel, and ruthenium have been used as the catalytically active metals. Cobalt and ruthenium have been found to be most suitable for catalyzing a process in which synthesis gas is converted to primarily hydrocarbons having five or more carbon atoms (i.e., where the $C_{5+}$ selectivity of the catalyst is high). Additionally, the catalysts often contain one or more promoters and a support or carrier material. Ruthenium is a widely used promoter.

The Fischer-Tropsch synthesis reactions are highly exothermic and reaction vessels must be designed for adequate heat exchange capacity. Because the feed streams to Fischer-Tropsch reaction vessels are gases, while the product streams include liquids, the reaction vessels must have the ability to continuously produce and remove the desired range of liquid hydrocarbon products. The first major commercial use of the Fischer-Tropsch process was in Germany during the 1930's. More than 10,000 B/D (barrels per day) of products were manufactured with a cobalt based catalyst in a fixed-bed reactor. This work was described by Fischer and Pichler in Ger. Pat. No. 731,295 issued Aug. 2, 1936.

Motivated by the hope of producing. of high-grade gasoline from; natural gas, research on the possible use of the fluidized bed for Fischer-Tropsch synthesis was conducted in the United States in the mid-1940s. Based on laboratory results, Hydrocarbon Research, Inc. constructed a dense-phase fluidized bed reactor, the Hydrocol unit, at Carthage, Texas, using powdered iron as the catalyst. Due to disappointing levels of conversion, scale-up problems, and rising natural gas prices, operations at this plant were suspended in 1957. Research continued, however, on developing Fischer-Tropsch reactors, such as slurry-bubble columns, as disclosed in U.S. Pat. No. 5,348,982. Despite significant advances, certain areas of the Fischer-Tropsch technology still have room for improvement. One potential technology in need of improvement relates to regeneration of the syngas catalyst.

After a period of time in operation, a catalyst will become deactivated, losing its effectiveness for synthesis gas conversion to a degree that makes it uneconomical at best and inoperative at worst. At this point, the catalyst can be either replaced or regenerated. Because the catalysts tend to be relatively expensive, regeneration is preferred over replacement. Catalyst systems can become deactivated by a number of processes, including coking, sintering, oxidation, and reduction. The process chiefly responsible for deactivation varies among catalyst systems. Therefore, the preferred method for regeneration tends to depend on the catalyst system to be regenerated.

Research is continuing on the development of more efficient Fischer-Tropsch catalyst systems and catalyst systems that can be more effectively regenerated. In particular, a number of studies describe the use of various gases, including hydrogen, air, and carbon monoxide to regenerate a variety of d-block metal containing Fischer-Tropsch catalyst systems.

U.S. Patent No. 3,958,957, issued on May 25, 1976, describes a carbon-alkali metal catalyst, used for conversion of synthesis gas to methane and higher hydrocarbons at a pressure of 100–1500 psig and a temperature of 300–550° F. at a typical gas hourly space velocity of 1000 volumes gas/hr/volume catalyst. The carbon-alkali metal catalyst can be regenerated with air oxidation.

U.S. Pat. No. 4,151,190, issued on April 24, 1979, describes a catalyst comprising at least one of a sulfide, oxide, or metal of Mo, W, Re, Ru, Ni, or Pt, at least one of a hydroxide, oxide, or salt of Li, Na K, Rb, Cs, Mg, Ca, Sr, Ba, or Th, and a support, used for conversion of synthesis gas with an $H_2$:CO ratio of 0.25–4.0, preferably 0.5–1.5, to $C_2$–$C_4$ hydrocarbons at a pressure of 15–2000 psia and a temperature of 250–500° C. at a typical gas hourly space velocity of 300 v/hr/v. This catalyst can be regenerated by contacting it with hydrogen gas at 500–600° C. for 16 hours.

U.S. Pat. No. 4,738,948, issued on Apr. 19, 1988, describes a catalyst comprising cobalt and ruthenium at an atomic ratio of 10–400, on a refractory carrier, such as titania or silica. The catalyst is used for conversion of synthesis gas with an $H_2$:CO ratio of 0.5–10, preferably 0.5–4, to $C_5$–$C_{40}$ hydrocarbons at a pressure of 80–600 psig and at a temperature of 160–300° C., at a gas hourly space velocity of 100–5000 v/hr/v. This catalyst can be regenerated by contacting it with hydrogen gas at 150–300° C., preferably 190–260° C., for 8–10 hours.

U.S. Pat. No. 5,728,918, issued on March 17, 1998, describes a catalyst comprising cobalt on a support, used for conversion of synthesis gas with an $H_2$:CO ratio of 1–3, preferably 1.8–2.2, to $C_5$+hydrocarbons at a pressure of 1–100 bar and at a temperature of 150–300° C. typical gas hourly space velocity of 1000–6000 v/hr/v. This catalyst can be regenerated by contacting it with a gas containing carbon monoxide and less than 30% hydrogen, at a temperature more than 10° C. above Fischer-Tropsch conditions and in the range 100–500° C., and at a pressure of 0.5–10 bar, for at least 10 minutes, preferably 1–12 hours. The contact time period depends on temperature and gas hourly space velocity. The 918 patent also teaches an activation procedure, which may include a first step of contacting the catalyst with a gas containing molecular oxygen, preferably air, at 200–600° C., at atmospheric pressure, for more than 30 minutes, and preferably for 1–48 hours.

U.S. Pat. No. 4,595,703, issued on June 17, 1986, describes a catalyst comprising cobalt or thoria promoted cobalt on a titania support, used for conversion of synthesis gas with an $H_2$:CO ratio of 0.5–4, preferably 2–3, to C,>hydrocarbons at a pressure of preferably 80–600 psi and at a temperature of 160–290° C., at a gas hourly space velocity of 100–5000 v/hr/v. This catalyst can be regenerated by contacting it with hydrogen gas, or a gas which is inert or non- reactive at stripping conditions such as nitrogen, carbon monoxide, or methane, at a temperature substantially the same as Fischer-Tropsch conditions. If it is necessary to remove coke deposits from the catalyst, the catalyst can be contacted with a dilute oxygen-containing gas, at oxygen partial pressure of at least 0.1 psig, at 300–550° C., for a time sufficient to remove coke deposits, followed by contact with a reducing gas containing hydrogen, at a temperature of 200–575° C. and at a pressure of 1–40 atmospheres, for 0.5–24 hours.

U.S. Pat. No. 4,585,798 issued on Apr. 29, 1986, describes a catalyst comprising cobalt and ruthenium in an atomic ratio greater than about 200:1 and, preferably, a promoter, such as a Group IIIB or IVB metal oxide, on an alumina support, used for conversion of synthesis gas to hydrocarbons at a pressure of preferably 1–100 atmospheres and at a temperature of 160–350° C., at a gas hourly space velocity less than 20,000 v/hr/v, preferably 100–5000 v/hr/v, especially 1000–2500 v/hr/v, which is activated prior to use by reduction with hydrogen gas, followed by oxidation with diluted air, followed by further reduction with hydrogen gas.

Despite the vast amount of research effort in this field, currently known methods of regeneration of Fischer-Tropsch catalysts are not always sufficiently effective for a particular catalyst system. In particular, it has been found that certain types of deactivated catalysts cannot be effectively regenerated by contacting them with hydrogen. Hence, there is still a great need to identify new regeneration methods, particularly methods that are effective for regenerating deactivated cobalt ruthenium catalyst concurrently with regenerating the catalyst, so as to maximize the regenerated catalyst activity and thus enhance the process economics.

SUMMARY OF THE INVENTION

This invention relates to a process and catalyst for producing hydrocarbons, and includes a method for catalyst regeneration. The Fischer-Tropsch synthesis process comprises contacting a feed stream comprising hydrogen and carbon monoxide with a catalyst in a reaction zone maintained at conversion-promoting conditions effective to produce an effluent stream comprising hydrocarbons.

The regeneration process comprises contacting a deactivated Fischer-Tropsch catalyst with a regeneration gas under regeneration-promoting conditions, for a period of time sufficient to reactivate the Fischer-Tropsch catalyst. More specifically, the regeneration-promoting conditions in accordance with the present invention include a temperature between about 250° C. and 350° C. and a pressure between about 0 psig (0.1 MPa) and about 350 psig (2.5 MPa). Contact with the regeneration gas is maintained for a period of time sufficient to reactivate the Fischer-Tropsch catalyst. The regeneration gas preferably comprises steam or steam and. hydrogen, with the hydrogen not exceeding 5% by volume of the total regeneration gas. The volume ratio of the regeneration gas to the deactivated Fischer-Tropsch catalyst is preferably at least about 3. It will be understood that in some instances the regeneration gas may be generated by passing a liquid through a heating zone before contact with the catalyst; and it will be further understood that references herein to regeneration gas include streams that may contain some liquid.

This invention further includes a process of cycling between the synthesis process and the regeneration process.

BRIEF DESCRIPTION OF THE DRAWINGS

For a more detailed descritption of the preferred embodiments of the present invention, reference will now be made to the accompanying drawings, in which like reference numbers indicate like features, wherein.

DETAILED DESCRIPTION OF THE INVENTION

Synthesis Reaction

Figure 1:
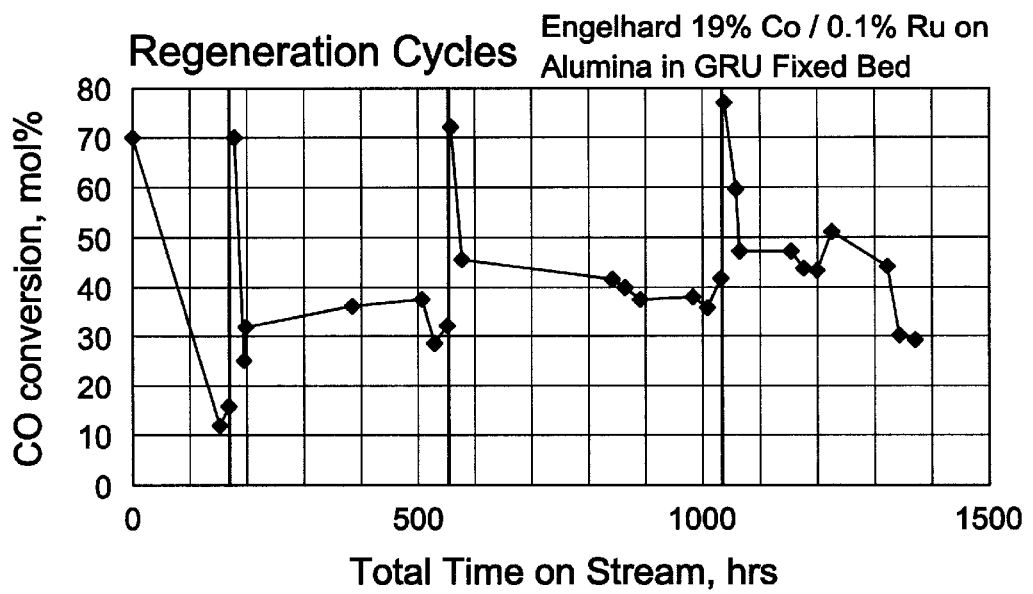
FIG. 1 is a plot of % CO conversion as a function of time illustrating exemplary regeneration of a catalyst with a regeneration gas containing steam.

The feed gases charged to the synthesis process that precedes the present regeneration process comprise hydrogen, or a hydrogen source, and carbon monoxide. $H_2$/CO mixtures suitable as a feedstock for conversion to hydrocarbons according to the synthesis process can be obtained from light hydrocarbons such as methane by means of steam reforming, partial oxidation, or other processes known in the art. Preferably the hydrogen is provided by free hydrogen, although some Fischer-Tropsch catalysts have sufficient water gas shift activity to convert some water to hydrogen for use in the Fischer-Tropsch process. It is preferred that the molar ratio of hydrogen to carbon monoxide in the feed be greater than 0.5:1 (e.g., from about 0.67:1 to 2.5:1). The feed gas stream may contain hydrogen and carbon monoxide in a molar ratio of about 2:1. The feed gas stream may also contain carbon dioxide. The feed gas stream should contain a low concentration of compounds or elements that have a deleterious effect on the catalyst, such as poisons. For example, the feed gas may need to be pre-treated to ensure that it contains low concentrations of sulfur or nitrogen compounds such as hydrogen sulfide, ammonia and carbonyl sulfides.

The feed gas is contacted with the catalyst in a reaction zone. Mechanical arrangements of conventional design may be employed as the reaction zone including, for example, fixed bed, fluidized bed, slurry phase, slurry bubble column, reactive distillation column, or ebulliating bed reactors, among others, may be used. The size and physical form of the catalyst may vary, depending on the reactor in which it is to be used.

Catalyst Support

The active catalyst components are carried or supported on a support selected from the group including silica, titania, titania/alumina, zirconia, alumina, aluminum fluoride, and fluorided alumina. Aluminum fluoride supports are defined as at least one aluminum fluoride (e.g., alpha-$AlF_3$, beta-$AlF_3$, delta-$AlF_3$, eta-$AlF_3$, gamma-$AlF_3$, kappa-$AlF_3$ and/or theta-$AlF_3$). Preferred supports include alumina and aluminum fluoride. Preferred aluminum fluoride supports are aluminum fluorides that are primarily alpha-$AlF_3$ and/or beta-$AlF_3$.

Fluorided alumina is defined as a composition comprising aluminum, oxygen, and fluorine. The fluoride content of the fluorided alumina can vary over a wide range, from about 0.001% to about 67.8% by weight. Preferred are fluorided aluminas containing from 0.001% to about 10% by weight fluorine. The remainder of the fluorided alumina component will include aluminum and oxygen. The composition may also contain a minor amount (compared to aluminum) of silicon, titanium, phosphorus, zirconium and/or magnesium.

The support material comprising fluorided aluminas and/or an aluminum fluoride may be prepared by a variety of methods. For example, U.S. Pat. Nos. 4,275,046 and 4,902,838 and 5,243,106 disclose the preparation of fluorided alumina by the reaction of alumina with a vaporizable fluorine-containing fluorinating compound. Suitable fluorinating compounds include HF, $CCl_3F$, $CCl_2F_2$, $CHClF_2$, $CH_2CHF_2$, $CCl_2FCClF_2$ and $CHF_3$. U.S. Pat. No. 5,243,106 discloses the preparation of a high purity $AlF_3$ from aluminum sec-butoxide and HF.

Metals can be supported on aluminum fluoride or on fluorided alumina in a variety of ways. For example, U.S. Pat. No. 4,766,260 discloses the preparation of metals such as cobalt on a fluorided alumina support using impregnation techniques to support the metal. U.S. Pat. No. 5,559,069 discloses the preparation of a multiphase catalyst composition comprising various metal fluorides including cobalt fluoride homogeneously dispersed with aluminum fluoride. PCT Int. Publ. No. 97/19751 discloses the preparation of multiphase catalyst compositions comprising metallic ruthenium homogeneously dispersed with various metal fluorides including aluminum fluoride.

Phases of aluminum fluoride such as eta, beta, theta and kappa can be prepared as described in U.S. Pat. No. 5,393,509, U.S. Pat. No. 5,417,954, and U.S. Pat. No. 5,460,795.

Aluminas that have been treated with fluosilicic acid ($H_2SiF_6$) such as those described in European Patent Application No. EP 497,436 can also be used as a support. The support disclosed therein comprises from about 0.5 to about 10 weight percent of fluorine, from 0.5 to about 5 weight percent of silica and from about 85 to about 99 weight percent of alumina.

Catalyst

Catalysts which are contemplated to be regenerated by the present method include any of the Fischer-Tropsch catalysts known in the art, such as cobalt, ruthenium, cobalt/ruthenium, cobalt/rhenium, iron, and nickel. In particular, the catalyst may include cobalt and ruthenium. The amount of cobalt and ruthenium present in the catalyst may vary widely. Typically, the catalyst comprises cobalt and ruthenium in an amount from about 1 to 50% by weight (as the metal) of the total weight of catalytic metal and support, preferably from about 1 to 30% by weight, and more preferably from about 1 to 25% by weight. Ruthenium is added to the support in a concentration sufficient to provide a weight ratio of elemental ruthenium to elemental cobalt of from about 0.001:1 to about 0.25:1, and preferably from about 0.001:1 to about 0.05:1 (dry basis).

The catalyst may also contain a promoter selected from the group consisting of boron, phosphorus, potassium, manganese and vanadium. The amount of promoter is added to the cobalt-ruthenium catalyst in a concentration sufficient to provide a weight ratio of elemental promoter to elemental cobalt of from about 0.00005:1 to about 0.5:1, and preferably from about 0.0005:1 to about 0.01:1 (dry basis).

Catalysts which may be regenerated by the present method may be prepared by any of the methods known to those skilled in the art. By way of illustration and not limitation, such methods include impregnating the catalytically active compounds or precursors onto a support, extruding one or more catalytically active compounds or precursors together with support material to prepare catalyst extrudates, and/or precipitating the catalytically active compounds or precursors onto a support. Accordingly, the supported catalysts of the present invention may be used in the form of powders, particles, pellets, monoliths, honeycombs, packed beds, foams, and aerogels.

The most preferred method of preparation may vary, as will be recognized by those skilled in the art, depending for example on the desired catalyst particle size. Those skilled in the art will be able to select the most suitable method for a given set of requirements.

One method of preparing a supported metal catalyst (e.g., a supported cobalt, cobalt/ruthenium, or cobalt/ruthenium/promoter catalyst) is by incipient wetness impregnation of the support with an aqueous solution of a soluble metal salt such as nitrate, acetate, acetylacetonate or the like. Another method of preparing a supported metal catalyst is by a melt impregnation technique, which involves preparing the supported metal catalyst from a molten metal salt. One preferred method is to impregnate the support with a molten metal nitrate (e.g., $Co(NO_3)_2.6H_2O$). Alternatively, the support can be impregnated with a solution of a zero valent metal precursor. One preferred method is to impregnate the support with a solution of zero valent cobalt such as $Co_2(CO)_8$, $Co_4(CO)_2$ or the like in a suitable organic solvent (e.g., toluene). Suitable ruthenium compounds are the common water soluble ones, e.g., ruthenium heptoxide ($Ru_2O_7$) and ammonium perruthenate ($NH_4RuO_4$).

The impregnated support is dried and reduced with hydrogen or a hydrogen containing gas. The hydrogen reduction step may not be necessary if the catalyst is prepared with zero valent cobalt. In another preferred method, the impregnated support is dried, oxidized with air or oxygen and reduced in the presence of hydrogen.

Typically, at least a portion of the metal(s) of the catalytic metal component (a) of the catalysts of the present invention is present in a reduced state (i.e., in the metallic state). Therefore, it is normally advantageous to activate the catalyst prior to use by a reduction treatment, in the presence of hydrogen at an elevated temperature. Typically, the catalyst is treated with hydrogen at a temperature in the range of from about 75° C. to about 500° C., for about 0.5 to about 24 hours at a pressure of about 1 to about 75 atm. Pure hydrogen may be used in the reduction treatment, as may a mixture of hydrogen and an inert gas such as nitrogen, or a mixture of hydrogen and other gases as are known in the art, such as carbon monoxide and carbon dioxide. Reduction with pure hydrogen and reduction with a mixture of hydrogen and carbon monoxide are preferred. The amount of hydrogen may range from about 1% to about 100% by volume.

Catalysis

The Fischer-Tropsch process is typically run in a continuous mode. In this mode, the gas hourly space velocity through the reaction zone may range from about 100 volumes/hour/volume catalyst (v/hr/v) to about 10,000 v/hr/v, preferably from about 300 v/hr/v to about 2,000 v/hr/v. The reaction zone temperature is typically in the range from about 160° C. to about 300° C. Preferably, the reaction zone is operated at conversion promoting conditions at temperatures from about 190° C. to about 260° C. The reaction zone pressure is typically in the range of about 80 psig (653 kPa) to about 1000 psig (6994 kPa), preferably from 80 psig (653 kPa) to about 600 psig (4237 kPa), and still more preferably from about 140 psig (1066 kPa) to about 400 psig (2858 kPa).

The products resulting from Fischer-Tropsch synthesis will have a range of molecular weights. Typically, the carbon number range of the product hydrocarbons will start at methane and continue to the limits observable by modern analysis, about 50 to 100 carbons per molecule. The catalyst of the present process is particularly useful for making hydrocarbons having five or more carbon atoms, especially when the above-referenced preferred space velocity, temperature and pressure ranges are employed.

Regeneration

The catalysts described above tend to become deactivated. They can be regenerated, and reactivated to restore their initial activity and selectivity, by contacting them with a regeneration gas comprising steam. The regeneration gas may further comprise hydrogen in an amount not exceeding 5% by volume of the total regeneration gas. Fischer-Tropsch synthesis conditions may be maintained, but preferably. the pressure is slightly reduced and the temperature is raised during regeneration. The temperature is preferably increased by an amount between 0° C. and 150° C. from the operating temperature of the Fischer-Tropsch synthesis. Regeneration temperatures can thus range from about 220° C. to about 450° C., preferably from about 250° C. to about 350° C., preferably between 260–300° C. Likewise, the pressure is preferably reduced by between 10 psig and about 300 psig from the pressure of the Fischer-Tropsch synthesis. Pressures can thus range from about 0 psig to about 350 psig. Contact between the regeneration gas and the catalyst is maintained for at least 5 minutes and preferably for at least 4 hours. At least 0.5 volumes, preferably at least 1 volume, and most preferably at least 3 volumes, of regeneration gas are used for each volume of catalyst.

Under these regeneration conditions, it has been found that the activity of certain catalysts will return to levels at or exceeding the pre-deactivation activity. In addition, it has been found that the level to which the activity of these catalyst drops as a result of deactivation may increase slightly over the first few regeneration cycles.

It is a surprising discovery of this invention that there is an optimal temperature range for the regeneration process of this invention. It has been discovered that at lower temperatures, the steam does not regenerate the catalyst. At high temperatures, the steam causes detrimental selectivity changes to the catalyst. Steam is an oxidizing agent that can oxidize cobalt metal sites on the catalyst to cobalt oxide, which is not catalytic for Fischer-Tropsch synthesis. There is significant literature stating that water or steam has a significant inhibiting effect on the Fischer-Tropsch reaction. Hence, it was expected that steam would deactivate the catalyst further. Contrary to these expectations, it has been discovered that there exists a temperature range in which contact with steam can cause an increase in catalytic activity. Depending on the catalyst and the degree of deactivation, it has been found that activity can be increased by at least 50% and sometimes as much as 700%.

While not wishing to be bound by any theory, it is believed that coking may be one mechanism that causes catalyst deactivation. Coking lays down a layer of carbon on the catalyst. Steam can regenerate coked catalyst through the reverse dissociative coking reaction:

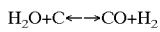

$$H_2O + C \leftarrow \rightarrow CO + H_2$$

It has been discovered that, by optimizing the temperature and pressure of the regeneration process, deactivated catalyst that may be coked can be effectively reactivated with steam, without adversely affecting its catalytic activity. If the primary deactivation mechanism is coking then steam will work in preference to hydrogen gas. Hydrogen gas may work better in cases where oxidation and sintering are the key mechanisms of deactivation.

It is believed that there are at least two general classes of catalyst where coking may be the key deactivation mechanism. The first class of catalyst is cobalt-containing supported catalysts where the support has high acidity. Acid site coking is well known in the art as a mechanism of the coking reaction. As an example, fluorided supports are highly acidic. The second class of catalyst is cobalt-containing catalysts having a high initial activity. A high initial activity occurs when the initial CO conversion is greater than about 60% or the initial $C_{5+}$ productivity is greater than 50 g $C_{5+}$/hr/kg catalyst. With high activity, the surface temperature on a catalyst particle can be very high, aiding in the coking mechanism.

EXAMPLE 1

A fixed bed reactor was used for the first example. The fixed bed was a 1 in. tubular reactor packed with 6 grams of catalyst and about 30 grams of diluent (glass beads). A thermocouple in the middle of the bed recorded the temperature. Synthesis gas with a ratio of about 2 $H_2/CO$ (mol/mol) was fed to the reactor such that the space velocity was about 2 standard liters of syngas/hr/gram of catalyst. The temperature during the reaction was held constant at about 225° C. The pressure was held constant at about 350 psig at the bed outlet. Two liquid products were obtained, the heavy waxy hydrocarbon (mostly $C_{20+}$) and a mixture of water and light hydrocarbon. A standard dry gas meter measured the off-gas rate. The composition of the off-gas was measured by gas chromatography. In the attached data, the catalyst was 19% Co, 0.1% Ru on Alumina. The catalyst average particle size was 20 microns.

With reference to FIG. 1, which shows the measured results, it can be seen that initially the catalyst activity produced a conversion of about 70%. The conversion fell fairly rapidly to 15% within 168 hours. At that point, the regeneration procedure was started. The feed was stopped and steam containing $H_2$ in the amount of 7% by volume was fed to the reactor. The steam was formed by vaporizing water in a line. Hydrogen gas was combined with the steam after vaporization. The W.H.S.V. was 5 grams water per gram catalyst per hour. The temperature in the reactor was maintained at about 300° C. The regeneration gas was fed for 4 hours. At the conclusion of the regeneration procedure, the regeneration gas was stopped. The temperature was lowered back to the reaction temperature of about 225° C. Syngas feed was resumed. The initial catalyst activity and selectivity as measured returned to the initial reaction. After about an additional 300 hours, the conversion fell to 32%. The catalyst was again regenerated in the manner described above. This procedure was repeated several more times. Regeneration was effective each time in the initial activity and selectivity.

In FIG. 1 the thick vertical lines inidicate the beginning of the regeneration procedure. The slight increase in activity level preceding each application of the regeneration procedure is not believed to be a general phenomenon. Causes might include slight adjustments in reaction conditions that occurred in some cases prior to regeneration. It can be seen in FIG. 1 that the activity after regeneration was at least 70% each time the catalyst was regenerated. The data in FIG. 1 suggest that the activity falls again less than 50 hours after regeneration. However, the data in FIG. 1 also suggest that the activity is raised to a higher baseline value after each regeneration procedure. One way to keep the activity closer to its post-regeneration value for a longer period of time is to utilize a continuous regenerator. In a continuous regenerator, the catalyst is sent into a regenerator vessel that continuously applies steam. Regenerated catalyst is cycled back into the reaction zone in the Fischer-Tropsch reactor online. Thus, the average time since last regeneration of the catalyst may be minimized. In this way, the Fischer-Tropsch synthesis operates at a level closer to, for example, the high conversion peaks of the graph shown in FIG. 1.

EXAMPLE 2

Figure 2:
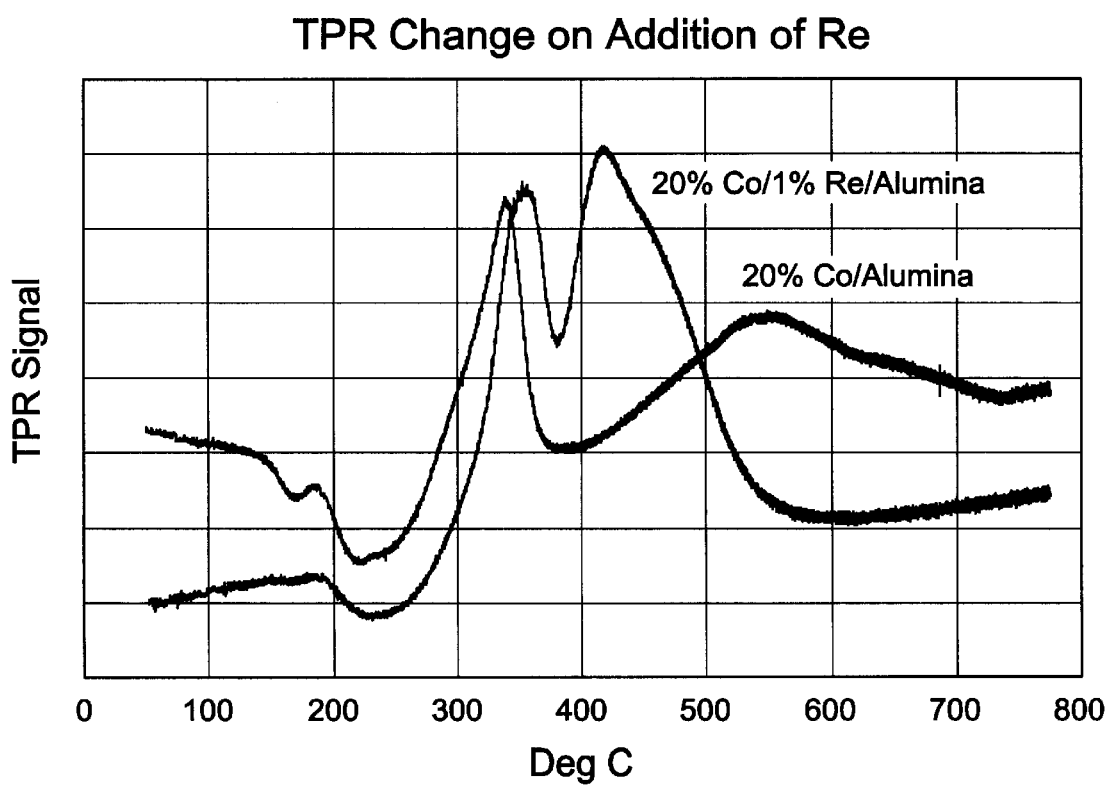
FIG. 2 is a plot of temperature programmed reduction signal as a function of temperature for exemplary catalysts.

A fixed bed reactor was used. The fixed bed was a 1 in. tubular reactor packed with 6 grams of catalyst and about 30 grams of diluent (glass beads). A thermocouple in the middle of the bed recorded the temperature. Synthesis gas with a ratio of about 2 $H_2$/CO (mol/mol) was fed to the reactor such that the space was about 2 standard liters of syngas/hr/gram of catalyst. The temperature during the reaction was held constant at about 225° C. The pressure was held constant at about 350 psig at the bed outlet. Two liquid products were obtained, the heavy waxy hydrocarbon (mostly $C_{20+}$) and a mixture of water and light hydrocarbon. A standard dry gas meter measured the off-gas rate. The composition of the off-gas was measured by gas chromatography. In the attached data, the catalyst was 19% Co, 0.1% Ru on Alumina. The catalyst average particle size was 20 microns. Regeneration was started after the feed was on stream for a duration of between about 500 and 1000 hours. The feed was stopped and a regeneration gas was fed to the reactor. The first three rows of Table 1 summarize results for a regeneration gas including about 93% steam and about 7% hydrogen gas. The last row of Table 1 summarizes results for a hydrogen gas as the regeneration gas. In the cases of a regeneration gas including 93% steam and 7% hydrogen gas, the steam was formed by vaporizing water in a line. The W.H.S.V. was about 5 grams water per gram catalyst per hour. Hydrogen gas was combined with the steam after vaporization. In each case, the regeneration gas was fed for 4 hours. The pressure of the reaction zone was maintained at about 50 psig during regeneration. At the conclusion of the regeneration procedure,. the regeneration gas was stopped. The temperature was lowered back to the reaction temperature of about 225° C. Syngas feed was resumed. The procedure was repeated, varying the hours the syngas feed was on stream in the range 500–1000 hours. The level of initial catalyst activity measured after regeneration, as the fraction of CO% conversion regained after a single regeneration is. measured is displayed in Table 1. In all the steam cases, selectivity to $C_{5+}$, and methane after regeneration was the same as the initial runs with the catalyst. However, in the case of $H_2$ gas at 350° C., the conversion increase that occurred after regeneration came almost entirely in the form of methane. This is consistent with either sintering of the Co particle during the regeneration or reactivation or activation of methane producing sites. Referring breifly to FIG. 2, a temperature of 350° C. was chosen for the attempt to regenerate the catalyst with $H_2$ gas because temperature programmed reduction experiments indicate that full reduction of catalyst from the oxide state to metal does not occur significantly below 350° C. In FIG. 2, results for two catalysts are shown, namely 20 wt. % Co, 1 wt. % Re on Alumina and 20 wt. % Co on Alumina. For each catalyst, the area under the curve indicates the total cobalt oxides or cobalt aluminates to be reduced. Referring again to Table 1, the poor performance of $H_2$ gas, a reducing agent, in regenerating the. catalyst at 350° C., suggests that catalyst oxidation is not a primary mechanism of catalyst deactivation for the catalysts studied.

TABLE 1

| Regeneration Gas | Temperature of Regeneration (° C.) | Fraction of Conversion Regained |
| --- | --- | --- |
| 93% steam/7% $H_2$ | 250 | 10 |
| 93% steam/7% $H_2$ | 300 | 95 |
| 93% steam/7% $H_2$ | 350 | 0 |
| $H_2$ gas (no steam) | 350 | 10 |

EXAMPLE 3

A slurry reactor was used. The catalyst particle size was about 20 microns in diameter. The impeller speed was 600 rpm during reaction and regeneration. The impeller acts to suspend the catalyst particles in the solution and keeps them from settling. Without the impeller, the catalyst would largely be at the bottom of the vessel and would not be in contact with the reactants or the regenerating gas. Further, the impeller acts as a gas mixing device. The type of impeller was a gas-inducing impeller configured to feed gas through a hollow shaft into the liquid. The impeller speed was chosen to be sufficiently high enough as to keep the catalyst in suspension and to break up large bubbles that may form by coalescence and thus keeps the interfacial area available for mass transfer from the gas to the liquid as high as possible. Slightly higher or lower impeller speeds do not significantly affect reactor performance. The maximum stable impeller speed in our system is about 1200 rpm, as higher speeds cause undesired vibrations. The catalyst was 20 wt % Co, 0.1 wt % Re on a fluorided alumina support. Suitable fluorided alumina supports are disclosed, for example, in co-pending application Ser. No. 09/314,921, commonly owned with the present application, and incorporated herein by reference. The slurry was approximately 15 wt % catalyst. The Fischer-Tropsch reaction was carried out at a pressure of about 350 psig (2.5 MPa) and a temperature of about 225° C. Table 2 shows that initially the catalyst activity produced a conversion of about 60%. The conversion fell fairly rapidly to 15% within 1014 hours. At that point, the regeneration procedure was started. The feed was stopped and steam containing about 5% $H_2$ by volume was fed to the reactor. The steam was formed by vaporizing water in a line. The W.H.S.V. was about 3 grams water per gram catalyst per hour. The temperature in the reactor was maintained at about 300° C. The pressure in the reactor was maintained at about 50 psig. The regeneration gas was fed for 4 hours. At the conclusion of the regeneration procedure, the regeneration gas was stopped. The temperature was lowered back to the reaction temperature of about 225° C. Syngas feed was resumed. The initial catalyst activity as measured was regained to 50%. The initial selectivity as measured returned to a level close to the initial level.

TABLE 2

| Time on Stream (hours) | CO Conversion (mole %) |
| --- | --- |
| 0 | 60 |
| 1014 | 15 |
| Post-regeneration | 50 |

Without further elaboration, it is believed that one skilled in the art can, using the description herein, utilize the present invention to its fullest extent. The embodiments described herein are to be construed as illustrative, and not as constraining the scope of the present invention in any way whatsoever. Furthermore, various modifications can be made without departing from the scope of the present invention. For example, while the present method has been described as a batch process, it will be understood that it can be carried out on a continuous basis, using known technologies for continuously treating catalyst.

The complete disclosures of all patents, patent documents, and publications cited herein are incorporated by reference in their entirety.

What is claimed is:

1. A process for regenerating a deactivated Fischer-Tropsch catalyst, comprising
    contacting the deactivated Fischer-Tropsch catalyst with a regeneration gas under regeneration-promoting conditions, for a period of time sufficient to reactivate the Fischer-Tropsch catalyst to a level of activity increased at least 50% as compared to the deactivated catalyst, wherein the regeneration gas comprises steam.

2. The process of claim 1 wherein the regeneration-promoting conditions include a temperature that is between 0° C. and 150° C. higher than the mean temperature of the Fischer-Tropsch synthesis in which the catalyst became deactivated.

3. The process of claim 1 wherein the regeneration-promoting conditions comprise a temperature between about 250° C. and about 350° C.

4. The process of claim 1 wherein the regeneration-promoting conditions comprise an average temperature about 300° C.

5. The process of claim 1 wherein the period of time is at least 4 hours.

6. The process of claim 1 wherein the volume ratio of the regeneration gas to the deactivated Fischer-Tropsch catalyst is at least about 0.5.

7. The process of claim 1 wherein the volume ratio of the regeneration gas to the deactivated Fischer-Tropsch catalyst is at least about 1.

8. The process of claim 1 wherein the volume ratio of the regeneration gas to the deactivated Fischer-Tropsch catalyst is at least about 3.

9. The process of claim 1 wherein the regeneration-promoting conditions comprise a pressure which is substantially the same as the mean Fischer-Tropsch synthesis pressure.

10. The process of claim 1 wherein the regeneration-promoting conditions comprise a pressure between about 10 psig and about 100 psig.

11. The process of claim 1 wherein the regeneration-promoting conditions comprise a pressure reduced by an amount between about 10 psig and about 300 psig from the mean pressure of the Fischer-Tropsch synthesis.

12. The process of claim 1 wherein the regeneration gas further comprises hydrogen in an amount not exceeding 10% by volume.

13. The process of claim 1 wherein the regeneration gas further comprises hydrogen in an amount not exceeding 1% by volume.

14. The process of claim 1 wherein the Fischer-Tropsch catalyst comprises a metal selected. from the group consisting of cobalt, ruthenium, cobalt/ruthenium, cobalt/rhenium, iron, and nickel.

15. The process of claim 14 wherein the Fischer-Tropsch catalyst further comprises a support selected from the group consisting of silica, titania, titania/alumina, zirconia, alumina, aluminum fluoride, and fluorided aluminas.

16. The process of claim 15 wherein the Fischer-Tropsch catalyst further comprises a promoter selected from the group consisting of boron, phosphorous, potassium, manganese, and vanadium.

17. The process of claim 1 wherein the Fischer-Tropsch catalyst comprises cobalt and ruthenium.

18. The process of claim 1 wherein the Fischer-Tropsch catalyst comprises cobalt and rhenium.

19. The process of claim 1 wherein the catalyst comprises an alumina support.

20. The process of claim 1, wherein the regenerated activity of the Fischer-Tropsch catalyst after regeneration is about 80% of the initial activity of the Fischer-Tropsch catalyst at the initial point in time of the Fischer-Tropsch synthesis in which the catalyst became deactivated.

21. A process for regenerating a deactivated Fischer-Tropsch catalyst, comprising:
    contacting the deactivated Fischer-Tropsch catalyst with a regeneration gas under regeneration-promoting conditions including a temperature between about 250° C. and 350° C. and at a pressure between about 10 psig and 350 psig, for a period of time sufficient to reactivate the Fischer-Tropsch catalyst to an activity level of 80% of the initial activity level prior to deactivation; the regeneration gas comprising steam and less than 10% by volume hydrogen; wherein the volume ratio of the regeneration gas to the deactivated Fischer-Tropsch catalyst is at least about 3.

22. A process for producing hydrocarbons, Comprising the steps of
    (a) carrying out a Fischer-Tropsch synthesis, comprising contacting a feed stream comprising hydrogen and carbon monoxide with a cobalt-containing catalyst in a reaction zone maintained at conversion-promoting conditions effective to produce an effluent stream comprising hydrocarbons until the activity of the catalyst drops to a first predetermined level,
    (b) carrying out a regeneration of deactivated Fischer-Tropsch catalyst, comprising
        contacting the deactivated Fischer-Tropsch catalyst with steam under regeneration-promoting conditions, for a period of time sufficient to reactivate the Fischer-Tropsch catalyst to a second predetermined level of activity, wherein the second predetermined level of activity is increased at least 50% over the first predetermined level of activity; and (c) cycling between steps (a) and (b), depending on the status of the catalyst.

23. The process of claim 22, wherein the catalyst is characterized by an initial predetermined level of activity prior to the first time step (a) occurs.

24. The process of claim 23, wherein the second predetermined level of activity is at least 80% of the initial predetermined level of activity.

25. The process of claim 22, wherein the first predetermined level of activity is less than about 25% of the initial predetermined level of activity.

* * * * *